United States Patent [19]

Miwa et al.

[11] Patent Number: 5,043,452
[45] Date of Patent: Aug. 27, 1991

[54] TITANIUM OR SILICON ATOM CONTAINING OXAZOLIDINE COMPOUND

[75] Inventors: Hiroshi Miwa, Itami; Yoshitaka Okude, Hirakata; Masakazu Watanabe, Toyonaka; Sakuichi Konishi, Ikoma, all of Japan

[73] Assignee: Nippon Paint Co., Ltd., Osaka, Japan

[21] Appl. No.: 458,372

[22] Filed: Dec. 28, 1989

[30] Foreign Application Priority Data

Aug. 28, 1989 [JP] Japan .................... 1-220604

[51] Int. Cl.$^5$ .................... C07D 263/04
[52] U.S. Cl. .................... 548/110; 548/106
[58] Field of Search .................... 548/106, 110

[56] References Cited

U.S. PATENT DOCUMENTS

| | | | |
|---|---|---|---|
| 3,435,046 | 3/1969 | Schoenewaldt | 548/110 |
| 3,937,716 | 2/1976 | Lewis et al. | 548/215 |
| 3,963,726 | 6/1976 | Pepe et al. | 548/110 |
| 4,002,637 | 1/1977 | Lewis et al. | |
| 4,043,956 | 8/1977 | Hutton et al. | |
| 4,518,787 | 5/1985 | Treadgold | 548/110 |
| 4,680,410 | 7/1987 | Wang | 548/110 |
| 4,772,716 | 9/1988 | Mülhaupt et al. | 548/110 |

FOREIGN PATENT DOCUMENTS 3088189  4/1988  Japan .................... 548/110

OTHER PUBLICATIONS

Chemical Abstracts, vol. 103, Dec. 1985, Columbus, Ohio, U.S.A.
S. Hsu Chang et al.
"Diethanolamine Degradation Under Gas-Treating Conditions" p. 483, Column 2, Abstract-No. 5322g.

*Primary Examiner*—Donald G. Daus
*Attorney, Agent, or Firm*—Wenderoth, Lind & Ponack

[57] ABSTRACT

Disclosed is a novel oxazolidine compound containing a titanium atom or a silicon atom. The ozazolidine compound is represented by the following formula [I];

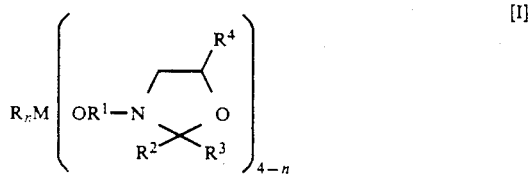

wherein R represents a hydrogen atom, a $C_1$–$C_{10}$ alkyl, an aryl group, a vinyl group, a $C_1$–$C_{10}$ halogen substituted alkyl group or a $C_1$–$C_{10}$ alkoxy group, M represents a silicon atom or a titanium atom, $R^1$ represents a $C_2$–$C_5$ alkylene group, $R^2$ and $R^3$ respectively represent a hydrogen atom, a $C_1$–$C_{10}$ alkyl group or an aryl group, $R^4$ represents a hydrogen atom or a methyl group and n is an integer of 0 to 3.

11 Claims, No Drawings

TITANIUM OR SILICON ATOM CONTAINING OXAZOLIDINE COMPOUND

BACKGROUND OF THE INVENTION

The present invention relates to a novel oxazolidine compound.

An oxazolidine ring-containing compound (hereinafter referred to as "oxazolidine compound") is easily hydrolyzed and produces two compounds. At least one of the product compounds is a compound which has a hydroxyl group, an amino group or an imino group. Thus, the oxazolidine compound is a compound which latently contains an active hydrogen and therefore suitable for a curing agent of a curable composition.

Oxazolidine compounds which are known to the art are generally represented as following;

$R^a$—[Oxazolidine ring]$_m$     (A)

wherein $R^a$ is an organic group and m is an integer. The compounds have different properties depending upon the organic group bonded to an oxazolidine ring (see Japanese Kokai Publication (unexamined) 116852/1976 corresponding to U.S. Pat. No. 4,043,956 and U.S. Pat. No. 4,002,637).

SUMMARY OF THE INVENTION

The present invention provides a novel oxazolidine compound which contains a titanium atom or a silicon atom. The oxazolidine compound is represented by the following formula [I];

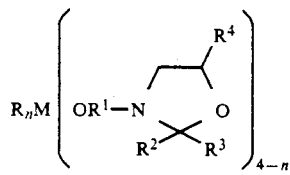

[I]

wherein R represents a hydrogen atom, a $C_1$–$C_{10}$ alkyl, an aryl group, a vinyl group, a $C_1$–$C_{10}$ halogen substituted alkyl group or a $C_1$–$C_{10}$ alkoxy group, M represents a silicon atom or a titanium atom, $R^1$ represents a $C_2$–$C_5$ alkylene group, $R^2$ and $R^3$ respectively represent a hydrogen atom, a $C_1$–$C_{10}$ alkyl group or an aryl group, $R^4$ represents a hydrogen atom or a methyl group and n is an integer of 0 to 3.

DETAILED DESCRIPTION OF THE INVENTION

In the above formula [I], it is preferred that R is a $C_1$–$C_5$ alkyl, more preferably methyl or ethyl and M is a silicon atom, $R^1$, $R^2$ and $R^3$ may be linear or branched. $R^2$ and $R^3$ are preferably methyl, ethyl, propyl, phenyl and the like.

The oxazolidine compound of the present invention may be prepared by reacting a compound represented by

$R_nMX_{4-n}$     [II]

[wherein R, n and M are the same as mentioned above, X is a halogen atom, such as chlorine, bromine and iodine], with a hydroxyoxazolidine compound having the formula [III];

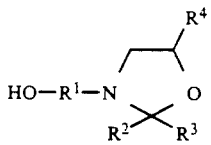

[III]

[wherein $R^1$–$R^4$ are the same as mentioned above.] The synthetic reaction is described as the following reaction formula;

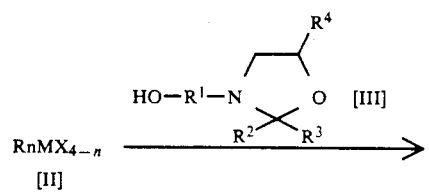

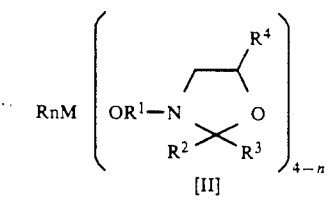

[wherein R, n, M, X and $R^1$–$R^4$ represent the same as mentioned above.]

The compound [II] is a halogeneated silane compound or a halogenated titanium compound. Typical examples of the halogenated silane compounds are methyltrichlorosilane, methyldichlorosilane, dimethyldichlorosilane, phenyltrichlorosilane, diphenyldichlorosilane, tetrachlorosilane, vinyltrichlorosilane, chloromethyltrichlorosilane, ethyltrichlorosilane, dimethoxymethylchlorosilane, diethoxydichlorosilane, triethoxychlorosilane and the like. Typical examples of the halogenated titanium compounds are tetrachlorotitanium and the like.

The hydroxyoxazolidine compound [III] includes 2-isopropyl-3-(2-hydroxypropyl)-5-methyloxazolidine, 2,2-dimethyl-3-(2-hydroxypropyl)-5-methyloxazolidine, 2-phenyl-3-(2-hydroxypropyl)-5-methloxazolidine, 2-isopropyl-3-(2-hydroxyethyl)oxazolidine, 2-methyl-2-isobutyl-3-(2-hydroxyethyl)oxazolidine, 3-(2-hydroxypropyl)-5-methyloxazolidine and the like. These compound [III] may be prepared by a known method, for example a method wherein an alkanol amine represented by

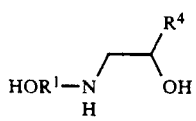

[IV]

[wherein $R^1$ and $R^4$ are the same as mentioned above.] is dehydration-condensed with an aldehyde or ketone represented by

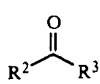

[V]

in a conventional acetal reaction condition. Examples of the amines [IV] are diisopropanolamine, diethanolamine and the like. Examples of the aldehydes or ketones [V] are isobutyl aldehyde, banzaldehyde, propion aldehyde, acetaldehyde, acetone, methyl ethyl ketone, methyl isobutyl ketone, cyclohexanone and the like.

A reaction of the compound [II] and the compound [III] may be generally effected at a temperature of less than 30° C. for 1 to 5 hours in a non-polar solvent in the presence of a base which traps produced hydrochloric acid. If the temperature is more than 30° C., the obtained compound [I] may decompose. The non-polar solvent may include hydrocarbons, such as n-hexane, n-heptane, benzene, xylene, toluene, n-octane, n-pentane and the like. The base can be pyridine, triethylamine and the like.

The reaction product is purified by a known purifying method, such as distillation and filtration to obtain the oxazolidine compound of the present invention. The oxazolidine compound may be colorless transparent liquid, but is not limited.

Since the oxazolidine compound [I] of the present invention contains a silicon or titanium atom which imparts hydrophobic properties, hydration by moisture in the air is inhibited and the compound [I] is more stable. The compound [I], as mentioned above, has a latent active hydrogen and can be useful for a curing agent of a polymer which contains a group reactive with the active hydrogen, such as a carboxyl group, a siloxy group, an isocyanate group and an acrylate group. Also, the compound has both a portion affinitive with an organic material and a portion affinitive with an inorganic material, and therefore can be used as a coupling agent.

EXAMPLES

The present invention is illustrated by the following examples which, however, are not construed as limiting the present invention to their details.

EXAMPLE 1

Synthesis of tris[3-(2-isopropyl-5-methyloxazolidinyl)-2-isopropoxy]methylsilane A reaction vessel equipped with a thermometer, a dropping funnel, a condenser having a water separator and a nitrogen introducing inlet was charged with 133 g of diisopropanolamine and 200 g of benzene, to which 75 g of isobutyl aldehyde was added dropwise at room temperature for 90 minutes. The content was heated to reflux and, after removing water produced during reacting, reacted for another 5 hours. Benzene was removed under a reduced pressure and then distilled as 85° to 90° C./1 mmHg to obtain 183 g of 2-isopropyl-3-(2-hydroxypropyl)-5-methloxazolidine.

Next, another reaction vessel equipped with a thermometer, a dropping funnel, a stirrer, a condenser and a nitrogen introducing inlet was charged with 183 g of the above obtained oxazolidine compound, 1,000 g of hexane and 103 g of triethylamine, to which 50 g of trichloromethylsilane was added dropwise at 0° C. for 2 hours in nitrogen atmosphere. It was then mixed at room temperature for 2 hours. The resultant solution was filtered and condensed to obtain 150 g of tris[3-(2-isopropyl-5-methyloxazolidinyl)-2-isopropoxy]methylsilane.

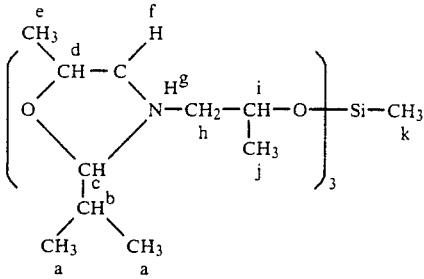

Colorless transparent liquid.
Infrared absorption spectrum: 1020, 1068, 1092, 1260, 1368, 1446, 2975 (cm$^{-1}$).
NMR spectrum (ppm): a; 1.25, b; 1.72, c; 4.09, d, i; 3.90, e; 0.98, f, g; 2.75, h; 2.42, j; 0.95, k; 0.15.

EXAMPLE 2

Synthesis of tetrakis[3-(2-isopropyl-5-methyloxazolidinyl)-2-isopropoxy]silane

The titled compound of 135 g was prepared as generally described in Example 1 with the exception that 43 g of tetrachlorosilane was employed instead of 50 g of trichloromethylsilane.

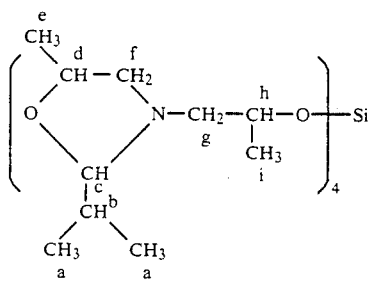

Colorless transparent liquid.
Infrared absorption spectrum: 1020, 1064, 1090, 1368, 1446, 2950 (cm$^{-1}$).
NMR spectrum (ppm): a; 1.25, b; 1.72, c; 4.09, d, h; 3.90, e; 0.98, f; 2.75, g; 2.42, i; 0.95.

EXAMPLE 3

Synthesis of bis[3-(2-isopropyl-5-methyloxazolidinyl)-2-isopropoxy]diphenylsilane The titled compound of 203 g was prepared as generally described in Example 1 with the exception that 124 g of dichlorodiphenylsilane was employed instead of 50 g of trichloromethylsilane.

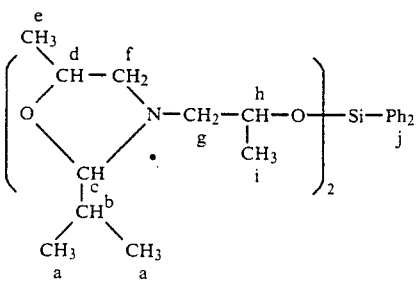

Colorless transparent liquid.

Infrared absorption spectrum: 700, 718, 740, 1014, 1066, 1122, 1368, 1452, 2970 (cm$^{-1}$).

NMR spectrum (ppm): a; 1.25, b; 1.72, c; 4.09, d, h; 3.90, e; 0.98, f; 2.75, g; 2.42, i; 0.95, j; 7.23, 7.60.

EXAMPLE 4

Synthesis of bis[3-(2-isopropyl-5-methyloxazolidinyl)-2-isopropoxy]dimethylsilane The titled compound of 145 g was prepared as generally described in Example 1 with the exception that 64 g of dichlorodimethylsilane was employed instead of 50 g of trichloromethylsilane.

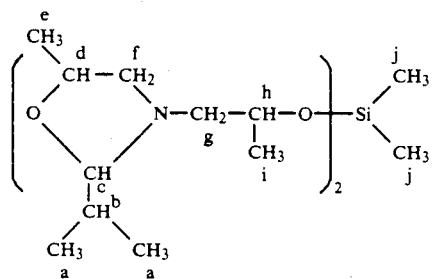

Colorless transparent liquid.

Infrared absorption spectrum: 794, 832, 886, 1012, 1068, 1096, 1258, 1368, 1446, 2940 (cm$^{-1}$).

NMR spectrum (ppm): a; 1.25, b; 1.72, c; 4.09, d, h; 3.90, e; 0.98, f; 2.75, g; 2.42, i; 0.95, j; 0.15.

EXAMPLE 5

Synthesis of bis[2-(2-isopropyloxazolidinyl)ethoxy]dimethylsilane

A reaction vessel equipped with a thermometer, a dropping funnel, a stirrer, a condenser having a water separator and a nitrogen introducing inlet was charged with 105 g of diethanolamine and 100 g of benzene, to which 75 g of isobutyl aldehyde was added dropwise at room temperature for 90 minutes. The content was heated to reflux and, after removing water produced during reacting, reacted for another 5 hours. Benzene was removed under a reduced pressure and then distilled at 75° to 79° C./1 mmHg to obtain 158 g of 2-isopropyl-3-hydroxyethyloxazolidine.

Next, another reaction vessel equipped with a thermometer, a dropping funnel, a stirrer, a condenser and a nitrogen introducing inlet was charged with 158 of the above obtained oxazolidine compound, 1,000 g of hexane and 103 g of triethylamine, to which 50 g of dichlorodimethylsilane was added dropwise at −10° C. for 2 hours in nitrogen atmosphere. It was then mixed at room temperature for 2 hours. The resultant solution was filtered and condensed to obtain 148 g of bis[2-(2-isopropyloxazolidinyl)ethoxy]dimethylsilane.

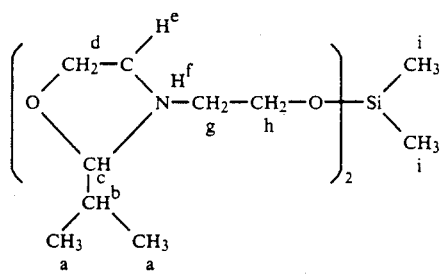

Colorless transparent liquid.

Infrared absorption spectrum: 798, 856, 1072, 1096, 1258, 1470, 2960 (cm$^{-1}$).

NMR spectrum (ppm): a; 1.25, b; 1.72, c; 4.09, d; 3.93, e; 2.65, f; 3.22, g; 2.42, h; 3.90, i; 0.15.

EXAMPLE 6

Synthesis of bis[3-(2-methyl-2-isobutyl-5-methyloxazolidinyl)-2-isopropoxy]dimethylsilane A reaction vessel equipped with a thermometer, a stirrer and a condenser having a water separator was charged with 133 g of diisopropanolamine, 100 g of benzene, 120 g of methyl isobutyl ketone and p-toluenesulfonic acid. The content was heated to reflux and reacted for another 5 hours with removing water. Benzene was removed under a reduced pressure and then distilled at 75° to 79° C./1 mmHg to obtain 152 g of 2-methyl-2-isobutyl-3-(2-hydroxypropyl)-5-methyloxazolidine.

Next, another reaction vessel equipped with a thermometer, a droppling funnel, a stirrer, a condenser and a nitrogen introducing inlet was charged with 152 g of the above obtained oxazolidine compound, 700 g of hexane and 73 g of triethylamine, to which 46 g of dichlorodimethylsilane was added dropwise at −10° C. for 2 hours in nitrogen atmosphere. It was then mixed at room temperature for 2 hours. The resultant solution was filtered and condensed to obtain 132 g of bis[3-(2-methyl-2-isobutyl-5-methyloxazolidinyl)-2-isopropoxy)dimethylsilane

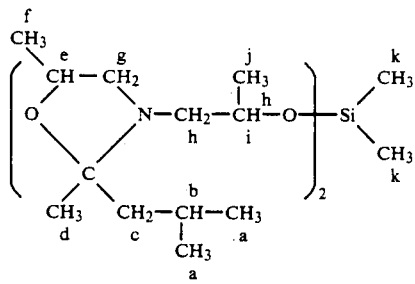

Colorless transparent liquid.

Infrared absorption spectrum: 796, 832, 886, 1014, 1088, 1258, 1372, 1450, 2960 (cm$^{-1}$).

NMR spectrum (ppm): a; 0.91, b; 1.40, c; 1.70, d; 1.30, e; 3.90, f; 0.98, g; 2.75, h; 2.42, i; 3.90, j; 0.95, k; 0.15.

EXAMPLE 7

Synthesis of tris[3-(2-phenyl-5-methyloxazolidinyl)-2-isopropoxy]methylsilane

A reaction vessel equipped with a thermometer, a dropping funnel, a stirrer and a condenser having a water separator was charged with 133 g of diisopropanolamine and 100 g of benzene, to which 107 g of benzaldehyde was added dropwise at room temperature for one hour. The content was heated to reflux and, after removing water produced during reacting, reacted for another 5 hours. Benzene was removed under a reduced pressure and then distilled at 125° to 127° C./1 mmHg to obtain 214 g of 2-phenyl-3-(2-hydroxypropyl)-5-methyloxazolidine.

Next, another reaction vessel equipped with a thermometer, a dropping funnel, a stirrer, a condenser and a nitrogen introducing inlet was charged with 214 g of the above obtained oxazolidine compound, 1,000 g of hexane and 90 g of triethylamine, to which 50 g of trichloromethylsilane was added dropwise at 0° C. for 2 hours in nitrogen atmosphere. It was then mixed at room temperature for 2 hours. The resultant solution was filtered and condensed to obtain 167 g of tris[3-(2-phenyl-5-methyloxazolidinyl)-2-isopropoxy]methylsilane.

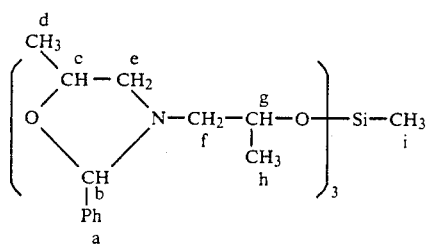

Colorless transparent liquid.

Infrared absorption spectrum; 679, 699, 758, 1022, 1058, 1083, 1260, 1369, 1442, 2930 (cm$^{-1}$).

NMR spectrum (ppm): a; 7.37, b; 4.61, c; 3.90, d; 0.98, e; 2.75, f; 2.42, g; 3.90, h; 0.95, i; 0.15.

What is claimed is:

1. An oxazolidine compound represented by the following formula [I]:

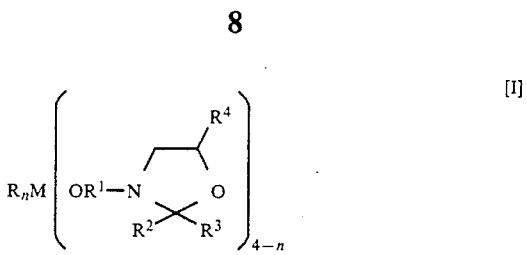

wherein R represents a hydrogen atom, a $C_1$-$C_{10}$ alkyl, a phenyl group, a vinyl group, a $C_1$-$C_{10}$ mono-halogen substituted alkyl group or a $C_1$-$C_{10}$ alkoxy group, M represents a silicon atom or a titanium atom, $R^1$ represents a $C_2$-$C_5$ alkylene group, $R^2$ and $R^3$ each represent a hydrogen atom, a $C_1$-$C_{10}$ alkyl group or a phenyl group, $R^4$ represents a hydrogen atom or a methyl group and n is an integer of 0 to 3 with the proviso than when R is vinyl, n is 1.

2. The oxazolidine compound according to claim 1 wherein R is methyl or ethyl.

3. The oxazolidine compound according to claim 1 wherein M is a silicon atom.

4. The oxazolidine compound according to claim 1 wherein $R^2$ and $R^3$ each methyl, ethyl, propyl or phenyl.

5. Tris[3-(2-isopropyl-5-methyloxazolidinyl)-2-isopropoxy]methylsilane.

6. Tetrakis[3-(2-isopropyl-5-methyloxazolidinyl)-2-isopropoxy]silane.

7. Bis[3-(2-isopropyl-5-methyloxazolidinyl)-2-isopropoxy]diphenylsilane.

8. Bis[3-(2-isopropyl-5-methyloxazolidinyl-5-methyloxazolidinyl)-2-isopropoxy]methylsilane.

9. Bis[2-(2-isopropyloxazolidinyl)ethoxy]dimethylsilane.

10. Bis[3-(2-methyl-2-isobutyl-5-methyloxazolidinyl)-2-isopropoxy]dimethylsilane.

11. Tris[3-(2-phenyl-5-methyloxazolidinyl)-2-isopropoxy]methylsilane.

* * * * *